US009814800B2

(12) United States Patent
Montenegro et al.

(10) Patent No.: US 9,814,800 B2
(45) Date of Patent: Nov. 14, 2017

(54) TISSUE DRESSING KIT

(71) Applicant: Medovent GmbH, Mainz (DE)

(72) Inventors: Rivelino Montenegro, Mainz (DE); Thomas Freier, Mainz (DE)

(73) Assignee: Medovent GmbH, Mainz (DE)

( * ) Notice: Subject to any disclaimer, the term of this patent is extended or adjusted under 35 U.S.C. 154(b) by 0 days.

(21) Appl. No.: 15/179,045

(22) Filed: Jun. 10, 2016

(65) Prior Publication Data

US 2016/0279284 A1 Sep. 29, 2016

Related U.S. Application Data

(62) Division of application No. 13/392,222, filed as application No. PCT/EP2010/062822 on Sep. 1, 2010.

(30) Foreign Application Priority Data

Sep. 1, 2009 (WO) ................. PCT/EP2009/006323

(51) Int. Cl.
A61L 26/00 (2006.01)
A61L 15/28 (2006.01)

(52) U.S. Cl.
CPC ........... A61L 26/0023 (2013.01); A61L 15/28 (2013.01); A61L 26/0066 (2013.01); A61L 2300/232 (2013.01); A61L 2300/404 (2013.01)

(58) Field of Classification Search
None
See application file for complete search history.

(56) References Cited

U.S. PATENT DOCUMENTS

| 4,532,134 | A | 7/1985 | Malette et al. |
| 4,572,906 | A * | 2/1986 | Sparkes ............... A61L 26/0052 106/135.1 |
| 5,013,769 | A | 5/1991 | Murray et al. |
| 8,303,980 | B2 | 11/2012 | Hirose et al. |
| 2001/0001788 | A1 | 5/2001 | Satoh et al. |
| 2001/0023259 | A1 | 9/2001 | Slabas et al. |
| 2003/0022573 | A1 | 1/2003 | Cintio et al. |
| 2003/0023216 | A1 | 1/2003 | Carlucci et al. |
| 2005/0042265 | A1 | 2/2005 | Guillot et al. |
| 2006/0159732 | A1 * | 7/2006 | Cullen ................... A61L 15/325 424/445 |
| 2006/0286156 | A1 | 12/2006 | Hirose et al. |
| 2009/0117213 | A1 | 5/2009 | Beaulieu et al. |
| 2010/0129423 | A1 * | 5/2010 | Freier ..................... A61L 27/20 424/426 |

FOREIGN PATENT DOCUMENTS

| EP | 0901795 | A2 | 3/1999 |
| EP | 1396514 | A1 | 3/2004 |
| GB | 2129300 | A | 5/1984 |
| JP | S598824 | A | 1/1984 |
| JP | 61172817 | A | 8/1986 |
| JP | H05504689 | A | 7/1993 |
| JP | 11146909 | | 6/1999 |
| JP | 2001055335 | A | 2/2001 |
| JP | 2001513367 | A | 9/2001 |
| JP | 2003530965 | A | 10/2003 |
| JP | 2005089372 | A | 4/2005 |
| JP | 2005225935 | A | 8/2005 |
| JP | 2006347999 | A | 12/2006 |
| JP | 2008161502 | A | 7/2008 |
| JP | 2008220388 | A | 9/2008 |
| JP | 2009528437 | A | 8/2009 |
| WO | WO-91/05574 | A1 | 5/1991 |
| WO | WO-9907416 | A1 | 2/1999 |
| WO | WO 01/41820 | * | 6/2001 ............. A61L 15/28 |
| WO | WO-0247737 | A1 | 6/2002 |

(Continued)

OTHER PUBLICATIONS

European Patent Office—Extended European Search Report for European Application No. 16181211.0 dated Nov. 24, 2016 (8 pages).
International Search Report and Written Opinion of the International Searching Authority for International Patent Application PCT/EP10/062822 dated May 17, 2011 (11 pages).
Minagawa, Tatsuya et al., "Effects of molecular weight and deacetylation degree of chitin/chitosan on wound healing", 2007 Carbohydrate Polymers 67 (pp. 640-644).
Kim, In-Yong et al., "Chitosan and its derivatives for tissue engineering applications," 2008 Biotechnology Advances 26 (pp. 1-21).
Office Action in corresponding Japanese Patent Application 2012-526085 dated Jan. 28, 2014 and English Translation (6 pages).
Office Action in corresponding Canadian Patent Application No. 2,771,365 dated Jan. 28, 2014 (3 pages).
Office Action in corresponding Canadian Patent Application No. 2,771,556 dated Feb. 14, 2014 (5 pages).

(Continued)

*Primary Examiner* — Brian Gulledge
(74) *Attorney, Agent, or Firm* — Harris Beach PLLC

(57) ABSTRACT

A kit comprising a tissue dressing material for being applied in contact with the tissue of a patient and a detachment solvent for removing the tissue dressing material from the tissue. A method of treating a tissue of a patient, the method comprising the steps of: applying a water-soluble tissue dressing material in contact with the patient's tissue; and applying an acidic detachment solvent to the tissue dressing material for removing the tissue dressing material from the tissue. A method of treating a tissue of a patient, the method comprising the steps of: applying a liquid tissue dressing material in contact with the patient's tissue; and applying a detachment solvent to the tissue dressing material for removing the tissue dressing material from the tissue. A method of treating a tissue of a patient, the method comprising the steps of: applying a water-soluble tissue dressing material in contact with the patient's tissue; and allowing the water-soluble tissue dressing material to convert into a form in which it is insoluble in water at neutral pH. And a solid material comprising a polymer salt and glycerol, the glycerol content being at least 10% of the polymer salt content by weight, for use in a method of treating a human or animal tissue.

2 Claims, 7 Drawing Sheets

(56) References Cited

FOREIGN PATENT DOCUMENTS

| WO | WO-2007103208 A2 | 9/2007 |
| WO | WO-2008072230 A1 | 6/2008 |
| WO | WO-2009028965 A1 | 3/2009 |
| WO | WO-2010010756 A1 | 1/2010 |
| WO | WO-2011026498 A1 | 3/2011 |

OTHER PUBLICATIONS

Liu, Xiao Fei, et al., "Antibacterial Action of Chitosan and Carboxymethylated Chitosan," Journal of Applied Polymer Science, vol. 79, pp. 1324-1335.

Japan Patent Office—Final Office Action for Patent Application No. 2012-525885 dated Jan. 6, 2015 (6 pages).

Canadian Intellectual Property Office—Office Action in Canadian Patent Application No. 2,771,556 dated Feb. 17, 2015 (4 pages).

European Patent Office—Office Action in European Application No. 10 748 093.1 dated Mar. 25, 2015 (6 pages).

pH (http://en.wikipedia.org/w/index.php?title=PH&oldid=661840429) (12 pages).

https://en.wikipedia.org/wiki/Ivory_(soap) (4 pages).

Japan Patent Office—Office Action and English Translation for JP Application No. 2015-112415 dated Jul. 1, 2016 (7 pages).

\* cited by examiner

TISSUE DRESSING KIT

CROSS-REFERENCE TO RELATED APPLICATIONS

This application is a divisional application of co-pending application Ser. No. 13/392,222, filed May 3, 2012, which is a national stage application under 35 U.S.C. §371 of PCT Application No. PCT/EP2010/062822, filed Sep. 1, 2010, which claims priority to and the benefit of PCT Application No. PCT/EP2009/006323, filed Sep. 1, 2009, which is incorporated herein by reference in its entirety.

FIELD OF THE INVENTION

The invention relates to kits comprising a tissue dressing material for being applied in contact with the tissue of a patient. It further relates to methods of treating a tissue of a patient, in which methods a tissue dressing material is applied in contact with the patient's tissue. The invention also relates to a solid material for use in a method of treating a human or animal tissue.

BACKGROUND OF THE INVENTION

The polysaccharide chitosan is the at least partially N-deacetylated derivative of chitin. Chitin can be found widely in the exoskeletons of arthropods, gels, crustaceans and the cuticles of insects. It is usually derived from such natural sources. Chitosan in general is synthetically prepared by hydrolysis of chitin, although it can also be naturally derived directly, e.g. from certain fungi in which it occurs. The different solubilities of chitin and chitosan in dilute acids are commonly used to distinguish between the two polysaccharides. Chitosan, the soluble form, can have a degree of acetylation (DA) between 0% and about 60%, the upper limit depending on parameters such as processing conditions, molecular weight, and solvent characteristics. While soluble in acidic aqueous media, chitosan precipitates at a pH of above 6.3.

Both chitin and chitosan are promising polymers for biomedical applications because of their biocompatibility, biodegradability and structural similarity to the glycosaminoglycans. For comprehensive reviews of potential applications of chitin and chitosan see, e.g., Shigemasa and Minami, "Applications of chitin and chitosan for biomaterials", Biotech. Genetic. Eng. Rev. 1996, 13, 383; Kumar, "A review of chitin and chitosan applications", React. Funct. Polym. 2000, 46(1), 1; and Singh and Ray, "Biomedical applications of chitin, chitosan and their derivatives", J. Macromol. Sci. 2000, C40(1), 69.

Chitin and chitosan have been held to be of particular promise in wound healing applications, early scientific reports on this subject dating back to 1970 when Prudden et. al. in "The discovery of a potent pure chemical wound-healing accelerator", Am. J. Surg. 1970, 119, 560 described the successful application of chitin powder on human wounds. The primary factor in the acceleration of wound healing was reported to be the presence of N-acetyl-D-glucosamine (in contrast to D-glucosamine) which is released from chitin due to enzymatic degradation by lysozyme, which is abundantly available in fresh and healing wounds.

The use of poly(N-acetyl-D-glucosamine), i.e. chitin, as a wound healing accelerator is disclosed in the U.S. Pat. No. 3,632,754. U.S. Pat. No. 4,532,134 discloses the application of chitosan solutions, powders, films, and mats to wounds. The claimed method asks for chitosan being between 42 to 100% deacetylated. Animal experiments using 78 to 92% deacetylated chitosan are disclosed that show acceptable results when the material is applied to wounds of dogs, while interference with early wound healing is observed when the material is used to cover wounds of rats.

In the U.S. Pat. No. 5,902,798 and the US patent application US 2001/0056079 degrees of acetylation of less than 25% are asked for. In experiments applying 16% acetylated chitosan, inferior stimulation of cell proliferation and wound healing were found in an in vitro model using human skin compared to chitosan/heparin materials.

The UK patent GB 2358354 B teaches a flexible polymeric film comprising at least 80% by weight of chitosan with a degree of acetylation between 12 and 30%. A slightly higher rate of wound healing compared to non-treated wounds was found. The relatively weak mechanical properties which necessitate the use of an epichlorhydrine crosslinker or silicon coating may constitute a disadvantage of this prior art material. The document also suggests washing off the film in saline solution after healing of the wound.

Azad et. al., "Chitosan membranes as a wound-healing dressing: Characterization and clinical application", J. Biomed. Mater. Res. 2004, 69B, 216, discloses the use of 25% acetylated chitosan for the fabrication of films and meshes (perforated films). The authors found that chitosan films cause an impaired wound healing in patients undergoing skin grafting as a result of blood clot formation underneath the film, while the use of meshes led to a more efficient removal of blood, resulting in faster healing with good epithelialization and without scar formation.

In the U.S. Pat. No. 7,482,503 a chitosan acetate foam is described for use as a hemorrhage control wound dressing for severe bleeding. The chitosan is required to be at least 70% deacetylated and in the examples, degrees of deacetylation between 85 and 93% are used.

The US patent application US 2005/042265 A1 discloses a hydrogel for skin repair, the hydrogel containing a maximum of 5% chitosan. The chitosan's degree of acetylation is required to be no greater than 40%, in particular between 2% and 6%. Finally, the international patent application WO 2008/128567 A1 discloses medical articles, including wound dressings, at least partially made of chitosan. The lowest degree of acetylation disclosed is 3%.

The German patent application DE 10 2007 038 125 A1 discloses an adhesive composition for gluing or fixing biological tissue. The composition comprises a 50 to 98% deacetylated polysaccharide, e.g. chitosan. Another component of the composition is a functionalized oligolacton. The two components are provided into separate chambers of a spraying apparatus.

The International patent application WO 2008/1128567 discloses the biodissolution of least a part of a medical device in a dilute acid. The part of the device is made of N-acetylchitosan with a degree of acetylation of more than 3% and less than 25%. The biodissolution of the part of the device is controlled by adjusting the pH of the aqueous medium in contact with the N-acetylchitosan part of the device to a value of equal or less than 6.0.

Problem to be Solved by the Invention

It is an object of the present invention to provide a kit for improving the treatment of the tissue of a patient, the kit comprising a tissue dressing material to be applied in contact with the tissue of the patient. The invention further aims to provide improved methods for treating a tissue of a patient.

Moreover, the invention seeks to provide a new material for use in a method of treating a human or animal tissue.

Solution According to the Invention

According to the invention, the problem is solved by providing a kit comprising: a tissue dressing material for being applied in contact with the tissue of a patient; and a detachment solvent for removing the tissue dressing material from the tissue.

The problem is also solved by a method of treating a tissue of a patient, the method comprising the steps of: applying a water-soluble tissue dressing material in contact with the patient's tissue; and applying an acidic detachment solvent to the tissue dressing material for removing the tissue dressing material from the tissue. The problem is further solved by a method of treating a tissue of a patient, the method comprising the steps of: applying a liquid tissue dressing material in contact with the patient's tissue; and applying a detachment solvent to the tissue dressing material for removing the tissue dressing material from the tissue. Moreover, the problem is solved by a method of treating a tissue of a patient, the method comprising the steps of: applying a water-soluble tissue dressing material in contact with the patient's tissue; and allowing the water-soluble tissue dressing material to convert into a form in which it is insoluble in water at neutral pH. Finally, the problem is solved by providing a solid material comprising a polymer salt and glycerol, the glycerol content being at least 10% of the polymer salt content by weight, for use in a method of treating a human or animal tissue.

In the context of the present invention, a "detachment solvent" is a liquid that can be applied to the tissue dressing material when it is in a solid or gel-like state and that can facilitate detachment of the tissue dressing material from the tissue, preferably by at least partly dissolving and/or swelling the tissue dressing material. The preferred detachment solvent can reduce the adherence of the tissue dressing material to the tissue. Thus, with the detachment solvent it can be avoided that the tissue is damaged during removal of the tissue dressing material, and in particular it can be avoided that when the tissue dressing material is removed, parts of the tissue beneath it that adhere to the tissue dressing material are torn away. Amongst other cases, this can be of great advantage where the tissue dressing material is applied to a wound as a wound dressing material, because wound tissue can be very sensitive to mechanical stress. With the invention, therefore, irritation or damage of the regenerating tissue due to adhesions to the wound dressing material being removed can be avoided.

The terms "dissolve" and "dissolution" in context with a polymer is meant to refer to a process of mass loss of a solid or gel-like polymer form without molecular weight decrease (i.e., without decrease in polymer chain length) due to solubility in an aqueous environment. This is to be distinguished from "degradation", which is the process of molecular weight decrease due to depolymerisation of a polymer. Advantageously dissolution and/or swelling can facilitate the removal of the tissue dressing material. It can be achieved with the invention that the tissue dressing material is partly or even entirely dissolvable.

The inventors have found that providing the tissue dressing material together with the detachment solvent in a kit can considerably improve compliance in the sense that the patient is less likely to attempt to separate the tissue dressing material from the tissue without previous application of the detachment solvent. The kit according to the invention can also prevent the user from applying another, unsuitable or possibly even harmful solvent.

The term "water-soluble" in the context of the present invention refers to a state of the tissue dressing material in which it is soluble in water at neutral pH. In one aspect, the invention exploits the inventor's finding that some liquid tissue dressing materials, such as chitosan solutions, as well as some water-soluble but solid or gel-like tissue dressing materials, such as chitosan salts, upon application to the patient's tissue can transform into a solid or gel-like state, in which they are only soluble in an acid liquid solvent. This transformation may, for example, occur due to evaporation of a constituent of the tissue dressing material upon contact of the tissue dressing material with air. It may also be a result of an interaction of the tissue dressing material with a body fluid and/or the tissue itself; for example the relatively high pH of blood and/or the attachment of proteins present in the blood to the tissue dressing material may induce the transformation. Alternatively or additionally, transformation may be achieved by applying a transformation medium, e.g. an aqueous alkaline solution, to the tissue dressing material. Advantageously, it can be achieved that after transformation the tissue dressing material remains in place under normal condition, e.g. when the tissue is cleaned under tap water (neutral pH) or when soap (alkaline) is applied, and detaches only upon application of the detachment solvent. Moreover, as a result of the transformation the adhesion of the tissue dressing to the tissue can be reduced, facilitating later removal with the detachments solvent. Also, the water uptake capacity of the tissue dressing material can be reduced as a result of the transformation, which is desirable in certain applications.

The inventors have found that the presence of glycerol in the solid material for tissue treatment can accelerate the transformation from a water-soluble state into a state in which the material is only soluble in an acid liquid solvent. For example, in the case of a native chitosan salt as a polymer salt, transformation can be accelerated from approximately one month to a mere week. Without limiting the invention to a specific theory, the inventors believe that the acceleration may be due to the glycerol's effect of disrupting the crystalline structure of the polymer salt. Advantageously, the faster transformation allows the beneficial effects of the transformation (i.e. for example that after transformation the tissue dressing material remains in place when the tissue is cleaned under tap water) to set in earlier.

The kit, the methods and the solid material according to the invention advantageously can be used for locally confined antibacterial treatment of a patient's tissue. Thereby, it can be exploited that the site where the tissue dressing material is applied and thus the antibiotic activity takes place can be well controlled in order to achieve only a local presence of the antibiotic activity.

The kit, the methods and the solid material according to the invention advantageously can be used for the treatment of acute wounds, chronic wounds, and burn wounds or other types of wounds. It can also be used to treat tissue affected by dermatosis, for example athlete's food disease and psoriasis. The tissue dressing material of the kit and methods according to the invention can be applied in wound coverings, for example band aids, gauzes, films and foams, and in support aids, for example bandages, support tights and plaster casts. The invention may advantageously be used to treat cuts and abrasions, nose bleeding, severely bleeding wounds, and external and internal wounds in general. Thus, the invention can be of use when surgery is performed on a patient. The invention can also be applied advantageously to treat acne, razor burn and insect bites as well as in cosmetic application such as face masks and peelings. Preferably, the tissue dressing material not only contacts the tissue to be treated but also tissue surrounding the tissue to be treated.

While the invention preferably is used for external wounds, it may also be applied to internal wounds. In a preferred method, the invention is used internally as a hemostatic agent to control bleedings during surgeries, or it is applied in the treatment of injuries or diseases that cause internal bleedings. In another preferred method, the invention is used internally to prevent or limit infections by exploiting the potential of the deacetylated native chitosan as polymeric antibiotic. In another preferred method, the wound dressing material of the kit and methods according to the invention is used in regions of the body that are difficult to reach or treat, such as orifices, the genital area, or parts of the body where wound healing can be delayed, due to limited exposure to air. In a particularly preferred method, the wound dressing material is applied in areas that are sensitive to the application of foreign-body materials and conventional wound dressings, such as mucosa. The material may be applied into or onto the wound. A patient in the context of the present invention can be a human or an animal.

PREFERRED EMBODIMENTS OF THE INVENTION

Preferred features of the invention which may be applied alone or in combination are discussed in the dependent claims and in the following description.

Preferably, the detachment solvent for removing the tissue dressing material from the tissue is an aqueous detachment solvent. Preferred detachment solvents include distilled water, aqueous solutions of ionic compounds, such as an aqueous sodium chloride solution, buffered solutions, such as an acetic acid/acetate buffered solution, as well as aqueous solutions of non-ionic compounds, such as an aqueous glucose solution. Advantageously, water as a solvent is less irritating to the skin than many organic solvents. While in principle, the aqueous detachment solvent according to the invention may in addition to water comprise one or more co-solvents other than water, e.g. an organic co-solvent such as isopropanol or another alcohol, the preferred detachment solvent is free of organic solvents, including alcohols, esters, alkanes, halogenated solvents, amines, amides. It may, however, frequently contain an organic acid; organic acids are not considered organic solvents in the context of the present invention.

The detachment solvent for removing the tissue dressing material from the tissue, in particular if it shall be removed by dissolution, preferably is acidic. This embodiment of the invention exploits the fact that the solubility of the tissue dressing material, at least in a particular state of the tissue dressing material, can be pH-dependent. Thus, advantageously the pH of the detachment solvent can be selected from a range in which the tissue dressing material is dissolvable to detach the tissue dressing material from the tissue. The preferred pH of the detachment solvent is below 7, more preferably below 6.5, more preferably below 6.3. Advantageously, at a pH below 6.3 the base-form of native chitosan, one of the preferred wound dressing materials, is dissolvable in an aqueous medium. More preferably, the pH of the detachment solvent is below 6, more preferably below 5.5, more preferably below 5. The pH of the detachment solvent preferably is above 3.5. Thereby, advantageously, irritation of the tissue due to high acidity of the detachment solvent can be avoided. More preferably, the pH of the detachment solvent is above 4, more preferably above 4.5.

A preferred detachment solvent comprises a surfactant, e.g. a polysorbate such as Tween. Alternatively or in addition in may comprise substituted or unsubstituted polyalkyleneoxides, such as polyethylene glycol or polyethylene glycol esters. It has been found that the presence of such additives can considerably facilitate detachment of the solid, gel-like or solidified liquid tissue dressing material.

The amount of detachment solvent provided in the kit is at least 5 times per weight, more preferably at least 50 times per weight of the amount of the constituent(s) of the tissue dressing material other than water or the chitosan provided in the kit. By providing a sufficient amount of detachment solvent, it can be avoided that the pH of the tissue dressing material solution falls under a certain threshold. For application, the detachment solvent may be sprayed or brushed or applied by means of a sponge, a spatula, a pipette or gauze. Accordingly, a preferred kit contains a sponge, a brush, a spatula, a pipette or gauze for applying the detachment solvent. The detachment solvent may for example be provided in a sealed bottle or a disposable pipette, or by means of gauze, a sponge or a gel soaked with the detachment solvent. It may also be provided in a spraying apparatus. The preferred spraying apparatus comprises a container for storing the detachment solvent. It may also comprise pressurised gas for expelling the detachment solvent.

If in relation to preferred formulations, properties and features of tissue dressing materials described below it is not specified whether they concern a solid, gel-like or liquid tissue dressing materials, it shall be assumed that they may apply equally to any of such materials. The preferred tissue dressing material is a polymer or a co-polymer, preferably comprising or consisting of a polysaccharide, for example a chitosan such as native chitosan.

The term "native chitosan", in the context of the present invention refers to the defined chemical entity chitosan, which is a poly(N-acetyl-D-glucosamine-co-D-glucosamine) copolymer or a poly(D-glucosamine) homopolymer. Any cross-linked or otherwise chemically modified chitosan is considered a chitosan derivative, having different properties than native chitosan. In the context of the present invention the term "native chitosan" includes both the chitosan base and chitosan in the form of a chitosan salt, dissolved or un-dissolved. When in the context of the present invention it is referred to "chitosan" in general, this can be any form, salt or base, of native chitosan or any derivative of a poly(N-acetyl-D-glucosamine-co-D-glucosamine) copolymer or a poly(D-glucosamine) homopolymer, cross-linked and/or otherwise modified. The preferred chitosan is native chitosan. One of the advantages of native chitosan is its high biocompatibility and bioactivity. The preferred tissue dressing material can be essentially non-degradable, as is for example the case for deacetylated chitosan as defined below, or it can be partly or entirely degradable, for example biodegradable.

The preferred tissue dressing material has an antibacterial property. Thereby, advantageously, a localized antibacterial treatment can be achieved, thereby avoiding a systemic antibacterial activity, i.e. an antibacterial treatment of regions of the patient's body where such treatment is not required and/or not desirable. The invention can thus reduce side effects and contribute to the swift recovery of the patient. A suitable tissue dressing material with antibacterial properties is chitosan, in particular native chitosan.

Advantageously, with chitosan as the tissue dressing material or a constituent of the tissue dressing material, a tissue dressing material can be provided that is essentially free of toxic compounds. The invention can reduce the risk of wound infections, by exploiting the antibiotic nature of chitosan, in particular native chitosan, as a natural polymeric antibiotic with no systemic but only topical activity. Preferably, the tissue dressing material comprises no additional preservative. The inventors have found that the antibacterial properties of chitosan are sufficient to provide for a satisfactory shelf life of the product. This is particularly advantageous in liquid tissue dressings, as many liquid tissue dressing available on the market contain preservatives which may have toxic effects and may induce tissue irritations or allergic reactions.

The preferred chitosan has a degree of acetylation (DA) of 40% or less, preferably 20% or less, preferably 10% or less. Preferably, the chitosan is deacetylated. Preferably, this is the only chitosan component of the tissue dressing material. In the context of the present invention the term "deacetylated chitosan" means that the chitosan's DA is less than 2.5%. This embodiment of the invention exploits the inventors' discovery that a significantly accelerated rate of wound healing can be achieved by applying a native chitosan material that is deacetylated, i.e. essentially free of N-acetyl-D-glucosamine subunits. This finding is surprising when considering the importance attributed to the N-acetylated form of D-glucosamine in wound healing applications, e.g. as described in the U.S. Pat. No. 3,632,754, supra. Furthermore, it has been suggested, e.g., in Izume et. al., "A novel cell culture matrix composed of chitosan and collagen complex", in: Chitin and chitosan, Amsterdam 1989, 653, that chitosan of a very low degree of acetylation may rather have cytostatic properties, as it inhibits cell proliferation due to an extremely high cell adhesion.

The DA can be obtained by means of $^1$H NMR spectroscopy as, e.g., disclosed in Lavertu et al., "A validated $^1$H NMR method for the determination of the degree of deacetylation of chitosan", J. Pharm. Biomed. Anal. 2003, 32, 1149. "Deacetylated native chitosan" in the context of the present invention refers to chitosan that is both native and deacetylated according to the above definitions. In a preferred tissue dressing material according to the invention, the deacetylated chitosan's or the deacetylated native chitosan's DA is 2% or less, preferably 1.5% or less, more preferably 1% or less, more preferably 0.5% or less. Advantageously, such extremely low degrees of acetylation can further improve the wound healing properties of the invention. Also, biodegradation can be further inhibited, avoiding tissue ingrowths and excessive adhesion of the tissue dressing material. Moreover, by virtue of the low DA of the deacetylated native chitosan, the tissue dressing material can be applied in practically non-lysozyme biodegradable form, which can contribute to preventing tissue ingrowths and undesired adhesion of the polymeric matrix to growing tissue.

Preferably, chitosan, more preferably native chitosan, is the main component of the tissue dressing material. In the context of the present invention, the expression "main component" with regard to the tissue dressing material and a type of chitosan (such as chitosan in general, deacetylated chitosan, native chitosan or deacetylated native chitosan) means that the respective type of chitosan makes up at least 50% by weight of the tissue dressing material. Thus, if e.g. the tissue dressing material is provided as a solid or gel-like film to be applied to the tissue, this film is required to be made up of the respective type of chitosan by at least 50% by weight. In the case of the liquid tissue dressing material, the expression "main component" with regard to the constituent(s) other than water in the aqueous mixture means that at least 50% by weight of the combination of all constituents other than water must be the respective type of chitosan. Also, as discussed further below, the tissue dressing may comprise a first layer, which layer is formed of the tissue dressing material, and another layer formed of another material, this other layer acting as a support. In such a case, according to the above definition, it would be the first layer but not the support layer that is required to be made up of the respective type of chitosan by at least 50% by weight. Note that material which the tissue dressing material takes up from a tissue, such as exudative fluid from a wound, is not considered a component of the tissue dressing material.

In one embodiment of the invention, the tissue dressing material is a solid or a gel preferably a hydrogel. Preferably, it is present in the form of a film. The preferred film has a smooth surface, preferably with an average roughness $R_a$ of 1 μm (micrometer) or less, more preferably 0.3 μm or less, more preferably 0.1 μm or less. Advantageously, a smooth surface can reduce the formation of mechanical anchoring to the tissue, thereby further facilitating removal of the tissue dressing material. Typically, the dried film is between 0.5 and 500 μm thick, preferably between 10 and 100 μm. It has a surface area sufficient to cover the tissue to be treated, such as a wound, and preferably also some of the surrounding tissue. Preferably, at least 70%, more preferably at least 90%, more preferably at least 95% by weight of the solid or gel-like tissue dressing material is chitosan, preferably native chitosan.

The preferred solid or gel-like tissue dressing material for being applied in contact with the tissue of the patient is at least partly water-soluble. In other words, at the time it is provided for being applied to the patent's tissue it can be dissolved at least partly in water at neutral pH. The tissue dressing material may for example be a polymer salt, e.g. the salt of a polysaccharide such as a chitosan salt, e.g. the salt of native chitosan or a chitosan derivative. It is an achievable advantage of this embodiment of the invention that the tissue dressing material adheres well to the tissue. Thereby, it can be avoided that the tissue dressing material prematurely detaches from the tissue. This embodiment of the invention advantageously exploits the fact that chitosan salt is soluble in an aqueous solvent of neutral pH. Thus, wet or pre-wetted tissue can liquefy the tissue dressing material's surface, providing for a durable contact with the tissue. Preferred salts are those derived from the dissolution of a polymer, preferably chitosan such as native chitosan, in a inorganic acid, such as hydrochloric acid, or an organic acid selected from the group of monobasic or multibasic organic acids having 2 to 12 carbon atoms and a first pKa value between 1 and 5, such as acetic acid, citric acid, lactic acid, malic acid, succinic acid, mandelic acid, oxalic acid, tartaric acid, ascorbic acid, etc. In an alternative embodiment of the invention the respective type of polymer, is present in the form of the chitosan base.

A preferred solid tissue dressing material entirely consists of chitosan, preferably native chitosan. Preferably, a polymer salt such as a polysaccharide salt, preferably a chitosan salt, preferably a salt of native chitosan makes up the main component of the solid or gel-like tissue dressing material. More preferably, at least 70%, more preferably at least 90%, more preferably at least 95% by weight of the solid or gel-like tissue dressing material is a polymer salt such as a polysaccharide salt, preferably a chitosan salt, preferably a salt of native chitosan. A preferred solid tissue dressing material entirely consists of a polymer salt such as a polysaccharide salt, preferably a salt of chitosan, preferably a salt of native chitosan.

In a preferred embodiment, the tissue dressing material comprises glycerol in addition to the polymer salt such as chitosan salt, e.g. native chitosan salt. The glycerol content preferably makes up least 10%, more preferably at least 15%, more preferably at least 20% by weight of the solid tissue dressing material's polymer salt content, more preferably chitosan salt content, by weight. The glycerol preferably is present at a concentration of more than 10%, more preferably more than 15%, more preferably more than 20% by weight. The glycerol preferably is present at a concentration of less than 60%, more preferably less than 45%, more preferably less than 30% by weight.

In another preferred embodiment of the present invention, the tissue dressing material for being applied in contact with the tissue of the patient is liquid. In general, after application, the liquid tissue dressing material will solidify, i.e. it will turn into a solid or a gel, for example a hydro-gel. In some embodiments of the invention, removal, preferably evaporation, of the solvent that was present in the liquid tissue dressing when it was applied causes or at least contributes to the solidification. Additionally or alternatively, solidification may be caused or contributed to by other factors such as chemical or physical cross-linking of polymeric components of the tissue dressing material.

Preferably, the liquid tissue dressing material is an aqueous mixture, e.g. a dispersion or a suspension, more preferably a solution, i.e. it comprises water as the mixture medium or solvent, respectively. Moreover, it may comprise a co-solvent, for example an alcohol such as isopropanol. This can have the advantage of faster evaporation of the solvent which in turn leads to faster solidification.

The solute or more generally the constituent(s) of the mixture that remain once the mixture medium is removed upon solidification of the liquid tissue dressing material preferably comprises, more preferably consists of a salt, more preferably a polymer salt, for example a chitosan salt such as the salt of native chitosan or the salt of a chitosan derivative. Preferred salts are those derived from the dissolution of a polymer, preferably chitosan such as native chitosan, in an inorganic acid, such as hydrochloric acid, or an organic acid selected from the group of monobasic or multibasic organic acids having 2 to 12 carbon atoms and a first pKa value between 1 and 5, such as acetic acid, citric acid, lactic acid, malic acid, succinic acid, mandelic acid, oxalic acid, tartaric acid, ascorbic acid, etc.

Preferably, chitosan, more preferably native chitosan, is the main component other than water of the liquid tissue dressing material. Preferably at least 70% by weight of the constituent(s) of the mixture other than water are a polymer, preferably a polysaccharide such as chitosan, preferably native chitosan. A particularly preferred mixture essentially only consists of a polymer, preferably a polysaccharide such as chitosan, preferably native chitosan, and water. The preferred mixture is acidic. The concentration of the polymer preferably is less than 15%, more preferably less than 10%, more preferably less than 5%, more preferably less than 2% by weight.

For application, the liquid tissue dressing material preferably is sprayed onto the tissue and the mixture medium or solvent subsequently is allowed to evaporate to form a solid or gel-like film. Typically the film is between 0.1 and 50 μm thick, preferably between 1 and 20 μm. It has a surface area sufficient to cover the tissue to be treated such as a wound, and, preferably, also some of the surrounding tissue. Accordingly, the preferred kit according to the invention that comprises a liquid tissue dressing material further comprises a spraying apparatus for spraying a liquid tissue dressing material onto the tissue of the patient. The preferred spraying apparatus comprises a container for storing the liquid tissue dressing material. It may also comprise pressurised gas for expelling the liquid tissue dressing material. The tissue dressing material can be provided in two or more liquid components that are mixed shortly before or during application of the liquid tissue dressing material to the tissue. In this case, the spraying apparatus may comprise several containers and/or the kit may comprise several spraying apparatus each containing one of the liquid components. Alternatively, the liquid tissue dressing material may be brushed onto the tissue or applied by means of a sponge, a spatula, a pipette or gauze. Accordingly, a preferred kit contains a sponge, a brush, a spatula, a pipette or gauze for applying the liquid tissue dressing material or at least a constituent of the liquid dressing material to the tissue.

After the liquid tissue dressing material or the solid or gel-like water soluble tissue dressing material is brought into contact with the tissue, and in the case of a liquid tissue dressing during or after solidification, it preferably is allowed to transform into a water-insoluble form, e.g. a chitosan base. This may be achieved through exposure of the tissue dressing material to air or by applying a transformation medium, e.g. an aqueous alkaline solution. Thereby, advantageously, it can be achieved that after transformation the tissue dressing material remains in place under normal condition, e.g. when the tissue is cleaned under tap water (neutral pH) or when soap (alkaline) is applied, but detaches only upon application of the detachment solvent. Subsequently, when the tissue dressing material shall be removed, e.g. to be replaced or at the end of a therapy, the detachment solvent is applied to facilitate detachment of the tissue dressing material from the tissue. The preferred kit in addition to the tissue dressing material and the detachment solvent also comprises the transformation medium.

The preferred tissue dressing material, in particular the preferred liquid tissue dressing material, is free of organic solvents such as alcohols, esters, alkanes, halogenated solvents, amines, amides. It may, however, frequently contain an organic acid; organic acids are not considered organic solvents in the context of the present invention.

A preferred kit according to the invention comprises both a solid or gel-like and a liquid tissue dressing material. In a preferred method according to the invention, first a liquid and subsequently a solid or gel-like tissue dressing material is applied to the patient's tissue. Preferably in this method, the solid or gel-like tissue dressing material is applied before the liquid tissue dressing material has solidified. The inventors have found that the liquid tissue dressing material can facilitate attachment of the solid or gel-like tissue dressing material to the target tissue. This is particularly true for water-soluble solid or gel-like tissue dressing materials and as compared to an alternative method in which the water-soluble solid or gel-like tissue dressing material is wetted with water before attachment. This is because the latter method has been found to frequently lead to an undesirable deformation of the solid or gel-like tissue dressing material, which deformation can be avoided by the application of the liquid tissue dressing material for attachment of the solid or gel-like tissue dressing material. Preferably, in this kit and method, the liquid tissue dressing material is one of the preferred liquid tissue dressing materials described herein.

Similarly, in this kit and method, the solid or gel-like tissue dressing material is one of the preferred solid or gel-like tissue dressing materials described herein. Preferably, the liquid tissue dressing material and/or the solid or gel-like tissue dressing material and the detachment solvent are provided in separate containers.

The tissue dressing material, solid, gel-like or liquid, in some embodiments of the invention is a mixture or a compound material comprising several constituents, in the case of a liquid tissue dressing material preferably several constituents other than water. Preferably, the tissue dressing material comprises at least one constituent other than water and chitosan. In one embodiment, the tissue dressing material comprises glycerol. This advantageously can accelerate the transformation of the tissue dressing material from a water-soluble to a form that is only soluble in an acidic medium.

In a preferred embodiment, the tissue dressing material comprises at least one pharmaceutically active and/or bioactive constituent other than chitosan. Suitable bioactive constituents may e.g. be proteins, peptides or derivatives thereof, nucleic acids or derivatives thereof, low molecular weight compounds active as drugs, such as antibiotics or anti-inflammatory drugs, or agonists or antagonists of the innate immune system, or stimulating or differentiating growth factors for stimulating or differentiating growth of at least one sub-type of cells, or resins with affinity to certain components to be extracted from a wound surface, or dissolved or dispersed compounds or polymers with decorative functions such as light absorbing, fluorescent or phosphorescent or light reflecting particles. Alternatively, or in addition, the tissue dressing material may comprise biological cells.

In one preferred embodiment of the invention, the tissue dressing material (solid, gel-like and/or liquid) comprises a pH-sensitive dye for visually indicating the pH at the site of the tissue where the tissue dressing material is applied. The pH can be used as a proxy for indicating the condition of the tissue covered by the wound dressing material. For example, it is known that the pH in a wound can indicate the wound's present phase within the wound healing process.

In a preferred embodiment of the invention, the tissue dressing material has a pH of below 6.3, preferably below 6, particularly preferably around 5 to 5.5. The preferred pH is above 4.0, more preferably above 4.5. It is an achievable advantage of this embodiment of the invention, that the pH is close to that of the surface of healthy skin, thereby avoiding irritation or damage of the tissue to which the tissue dressing material is attached. This embodiment of the invention preferably applies to external applications of the tissue dressing material.

In a preferred embodiment of the invention, the tissue dressing material has a pH below 8.5, preferably below 8, particularly preferably around 7 to 7.5. The preferred pH is above 6.0, more preferably above 6.5. It is an achievable advantage of this embodiment of the invention, that the pH is close to that of healthy tissue, thereby avoiding irritation or damage of the tissue to which the tissue dressing material is attached. This embodiment of the invention preferably applies to internal applications of the tissue dressing material.

The preferred tissue dressing material has a water uptake capacity of less than 1500% by weight, more preferably less than 100%, more preferably less than 80%. Thereby it is advantageously achievable that a degree of humidity that is favourable for wound healing can be maintained under tissue dressing material as applied to a wound site. Preferably, the tissue dressing material in a solid or gel-like form has a water-uptake capacity of more than 25%, more preferably more than 50%. Advantageously this embodiment of the invention is suitable for absorbing exudative fluids and toxants. In a particularly preferred embodiment of the invention, the water-uptake capacity of the tissue dressing material is between 65 and 75%.

In a preferred embodiment of the invention, the tissue dressing material is transparent, in particular in the solid, gel-like or solidified form. In a kit that comprises both a solid or gel-like and a liquid tissue dressing material, preferably both the solid or gel-like tissue dressing material and the liquid tissue dressing material after solidification are transparent. Advantageously, this can make it easier for a physician to inspect the tissue treated with the tissue dressing material, in particular if it is a wound tissue. In some embodiments, the material is a transparent solid film. In others it is a mixture such as a dispersion, a suspension or a solution that forms a transparent film when applied to the tissue. Also, in the case that the tissue dressing material comprises a pH-sensitive dye the colour of the dye can be judged due to the transparency of the tissue dressing material.

In a preferred embodiment of the invention, the tissue dressing material is part of a tissue dressing that comprises a first layer, which layer is formed of the tissue dressing material, and at least another layer formed of another material, this other layer acting as a support. In particular, the support advantageously can help preventing premature detachment of the tissue dressing material from the tissue. The support preferably is located at the side of the layer of the tissue dressing material opposite to the side that is in contact with the tissue. Preferably, the support is adjacent to the tissue dressing material. The support according to the invention is particularly advantageous if the respective type of chitosan, preferably deacetylated native chitosan, is provided in the tissue dressing material in the form of the chitosan base, as the chitosan base in general adheres less well to tissue than a chitosan salt containing tissue dressing material. The support may for example be a woven fabric, foam or a perforated film. The support may for example be of natural materials such as cotton or a natural or synthetic polymer. Suitable polymers include biodegradable polymers, such as polyesters, polyorthoesters, polycarbonates, polyanhydrides, polyurethanes, polyphosphazenes, polyphosphoesters, polysaccharides, polypeptides, as well as derivatives, copolymers, and blends based on these polymers. Suitable polymers also include biodissolvable polymers, such as polyvinyl alcohol, polyvinyl acetate, poly-N-vinyl pyrrolidone, polyethylene glycol, polypropylene glycol, polysaccharides, polypeptides, as well as derivatives, copolymers, and blends based on these polymers. Furthermore, the support may consist of a non-biodegradable/non-biodissolvable polymer, such as silicones, polyurethanes, polyethylene terephthalate, polytetrafluorethylene, polysulfones, polyethersulfones, polyether ether ketones, polycarbonates, polymethacrylates, polysaccharides, polypeptides, as well as derivatives, copolymers, and blends based on these polymers.

A preferred tissue dressing according to the invention comprises a first layer, which layer is formed of the tissue dressing material, and another layer formed of another material, this other layer acting as an at least partial moisture barrier. In other words the other layer can prevent or at least delay the evaporation of water in the tissue dressing material during treatment of the tissue with the tissue dressing material according to the invention. This can be of particular advantage when the tissue dressing is applied to dry wounds.

The other layer preferably is located at the side of the layer of the tissue dressing material opposite to the side that is in contact with the tissue. Preferably, the other layer is adjacent to the tissue dressing material. The invention also encompasses tissue dressings that have both a support layer and another layer that acts as an at least partial moisture barrier. Of course both functions, that of a support and that of an at least partial moisture barrier, can also be fulfilled by a single other layer. The other layer may for example be of silicone or another polymer or polymer composition from the groups of polymers listed above. Typically the other layer is between 10 and 1000 μm thick, preferably between 50 and 500 μm. In some embodiments of the invention, the other layer is perforated. The holes of the perforation typically are between 10 and 1500 μm in diameter, preferably between 50 and 1000 μm. In an alternative embodiment of the invention, instead of the moisture barrier a layer is provided that can take up fluid, e.g. wound exudate. A suitable material may for example be polysaccharide-based hydrogels or hydrocolloids including cellulose derivatives, or polyurethane foams. This can be of particular advantage when the tissue dressing is applied to wet wounds.

In a preferred embodiment of the invention, the tissue dressing material, preferably the entire tissue dressing, is provided in a container that can prevent transformation of the tissue dressing material from its liquid or water-soluble state to its water-insoluble state as long as it is in the container and the kit's shelve life has not yet expired. Preferably, the container is vapour proof, more preferably it is essentially airtight.

Moreover, in some embodiments of the invention, the tissue dressing material on its side which is intended to be applied in contact with the patient's tissue is covered with a strippable cover sheet. The cover sheet is vapour proof, more preferably air-impermeable. This can contribute to preventing premature transformation of the tissue dressing material from its liquid or water-soluble state to its water-insoluble state before it is applied to the patient's tissue.

The tissue dressing material according to the invention in particular can exhibit one or a combination of the following advantageous properties: transparency; neutrality of odor; adhesion to the tissue to which it is applied; permeability for gas, in particular oxygen; locally confined antibiotic properties; hemostatic properties; regulation of humidity; and dissolvability at moderate pH. It may be non-cytotoxic, non-cytostatic and non-inflammatory. The material may inhibit or, alternatively, promote the growth cells of the tissue treated. It may also act as a barrier to protect from bacterial infection from inside and outside the tissue treated and as a mechanical protection. In particular it may protect and cover superficial wounds, lesions, abrasions that are at risk of infection, and burns. The tissue dressing material and the tissue dressing according to the invention can provide protection in cases where conventional wound dressings prove ineffective or are at least less effective, such as in the treatment of ulcerous tissue, wounds caused by viruses which tend to become ulcerous, mucosal tissue, the genital area, and body cavities. The material can be suitable for sterilization; it may be coloured with a dye;

The wound dressing material, in particular the liquid wound dressing material according to the invention may be free of aseptic agents, antioxidants and surfactants, thereby reducing the risk of toxic or allergic reactions. It may be pH-neutral to the skin, exhibiting a pH between 4 and 6, preferably around 5.5. It may be suitable for inhalation or for internal application by injecting or swallowing the material.

In particular, the liquid tissue dressing material according to the invention can exhibit one or a combination of the following advantageous properties: it may be water-based, free of organic solvents; have film-forming properties; be removable with an aqueous solution. It can be applied to areas of the human or animal body that are difficult to reach or where it is difficult to apply a solid material such as a film.

BRIEF DESCRIPTION OF THE DRAWINGS

The invention is illustrated in greater detail with the aid of the following figures.

DETAILED DESCRIPTION OF EMBODIMENTS OF THE INVENTION

1. $^1$H NMR Spectroscopy

Figure 1:
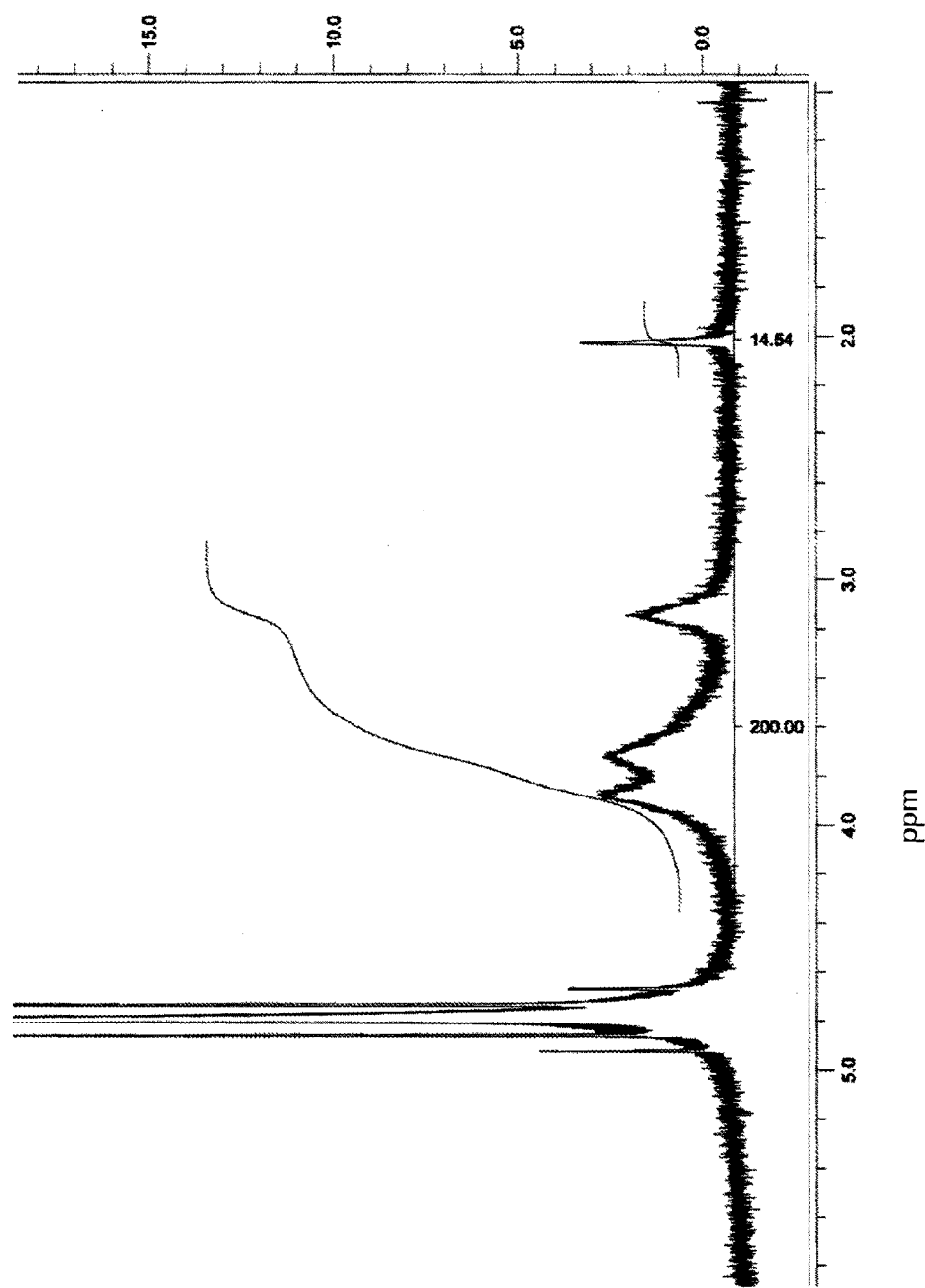
FIG. 1 shows an $^1$H NMR spectrum of native chitosan as purchased.
Figure 2:
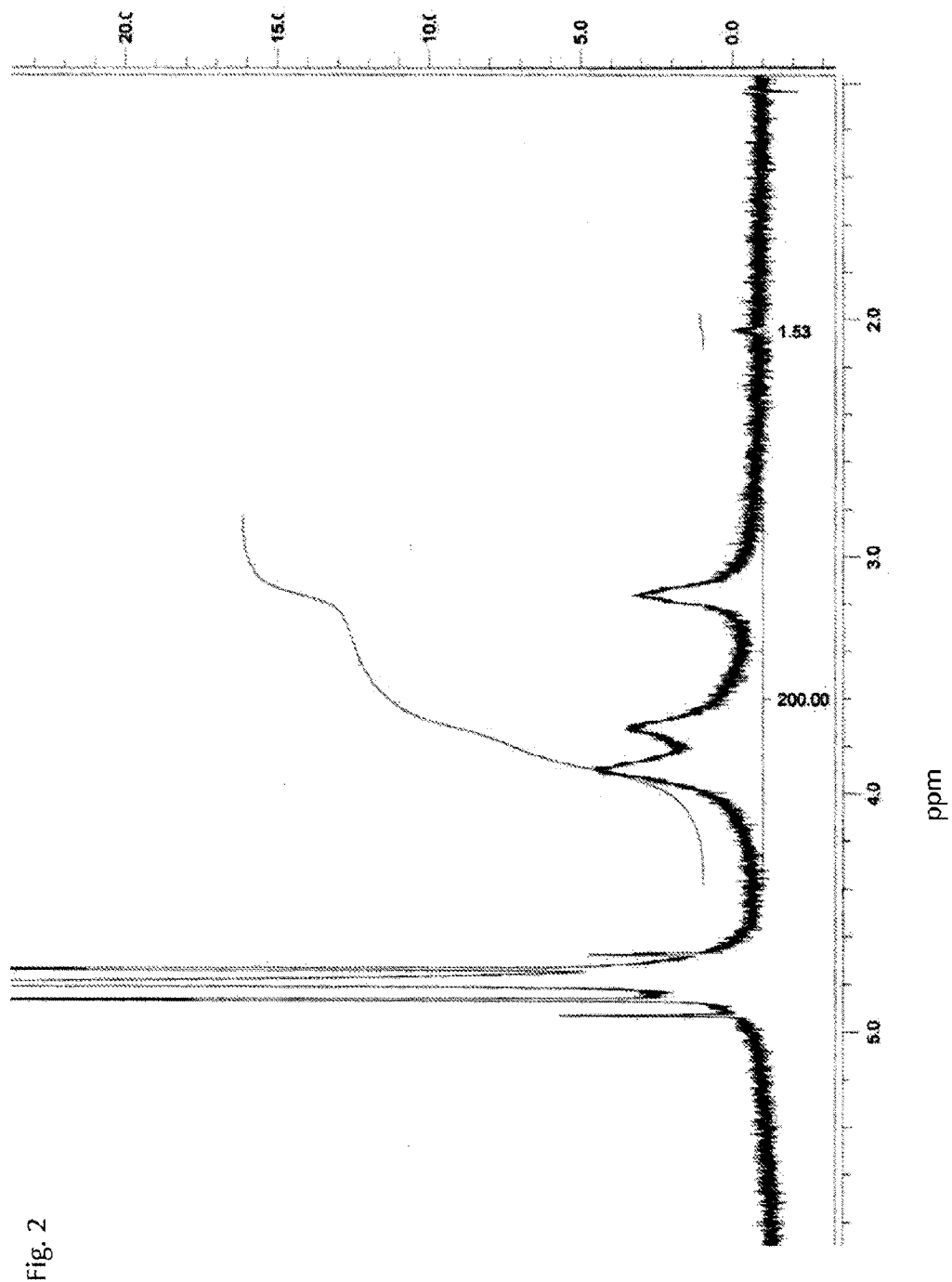
FIG. 2 shows an $^1$H NMR spectrum of native chitosan essentially deacetylated after further hydrolysis steps.

The chitosan used as a starting material in the examples below was obtained in the form of fine flakes from Cognis (Germany). The degree of acetylation (DA) was determined by $^1$H NMR spectroscopy. FIG. 1 shows an $^1$H NMR spectrum obtained from this commercially available chitosan. FIG. 2 shows a corresponding $^1$H NMR spectrum obtained from chitosan deacetylated after further hydrolysis steps applied to the commercial product as described further below. In both cases, chitosan was analyzed in a mixture of 0.25% DCI in $D_2O$ at a chitosan concentration of approximately 0.5% (w/v). The spectra were recorded using a Bruker AC200 spectrometer. NMR chemical shifts (δ, in ppm) were referenced to the signal of HDO (δ=4.8 ppm). The DA, calculated by comparing the integrated area under the peaks associated with H2-H6 of the D-glucosamine subunit with that of the methyl group, was determined as 14.5% for the native chitosan as purchased, and 1.5% for the deacetylated native chitosan.

2. Synthesis of Low-DA Chitosan

For further hydrolysis, 50 g (grams) of the chitosan flakes as obtained from the supplier Cognis were placed in a glass container, and 500 g of a 45% aqueous sodium hydroxide solution were added. The glass container was well shaken to mix the components, and placed in an oven for 2 hours at 100° C. It was then removed from the oven, and 500 mL (milliliters) of distilled water were added. The mixture was filtered through a glass frit. Then, the chitosan was washed with distilled water until the pH of the filtrate reached 6.5, and dried at 100° C. for 4 h (hours). This hydrolysis treatment was then repeated, resulting in 42 g of deacetylated native chitosan having a DA of 1.5% as determined by 1H NMR spectroscopy.

3. Cell Viability on Low-DA Chitosan

Human HaCaT keratinocytes were cultured in serum-free medium (Gibco) supplemented with 0.2 ng/mL (nanograms per milliliter) rEGF and 25 µg/mL (micrograms per milliliter) bovine pituitary extract. The calcium concentration was adjusted to 0.02 mM and the pH to 7.2-7.4. Cells were seeded at a density of $1\times10^6$ cells per 20 mL medium and incubated at 37° C. in air containing 10% $CO_2$. Cells were passaged once per week, and passages 20-25 were used for analysis.

Figure 3:
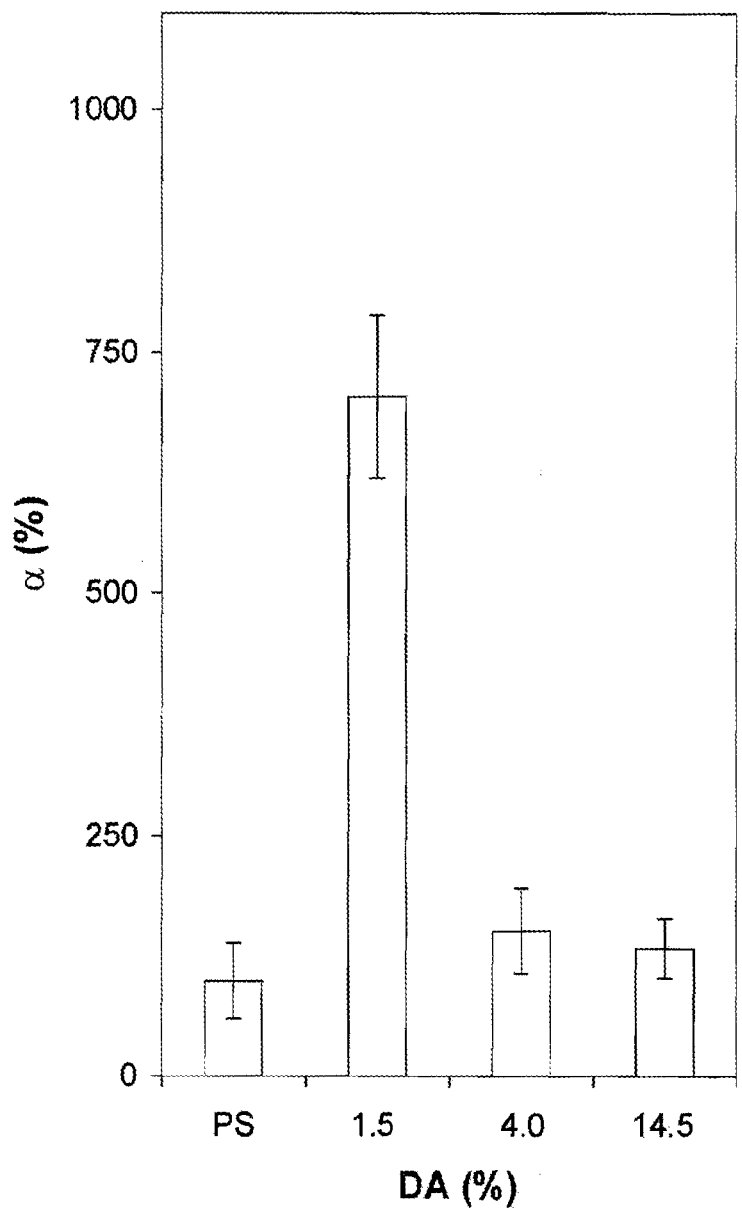
FIG. 3 illustrates the cell viability of keratinocytes on chitosan materials of various degrees of acetylation, relative to tissue culture polystyrene controls (PS=100%)

Chitosan films having DAs of 1.5, 4.0, and 14.5%, respectively, were placed in 24-well cell culture plates, and human HaCaT keratinocytes were seeded at a density of $5\times10^4$ cells per $cm^2$ and cultured for 2 days. Cell viability was determined using the MTS assay (Promega). After 4 h of MTS incubation with the cells, the light absorbance at 490 nm was measured by an ELISA plate reader and subtracted from that of the controls (without cells) to yield the corrected absorbance. Five samples of each DA were studied. FIG. 3a shows the relative light absorbencies a at 490 nm (PS=100%) for the three samples and a control using polystyrene (PS).

4. Preparation of a Solution of the Tissue Dressing Material (Material A)

7.5 g of the thus obtained native chitosan having a DA of 1.5% were dissolved in 500 mL of a 0.5% aqueous acetic acid by gently shaking for 24 h. A portion of the solution was filtered first through a glass fiber filter (pore size approximately 1 µm), and then through a 0.22 µm filter for sterilization, resulting in a solution of a tissue dressing material essentially consisting entirely of deacetylated native chitosan. Below, the material is referred to as tissue dressing material A.

5. Preparation of a First Example of a Solid Film-Type Tissue Dressing Material (Material B)

Two portions of 144 mL each of the non-filtered solution of deacetylated native chitosan prepared above were poured into two square-shaped moulds, $24\times24$ $cm^2$ (square centimeters) in size, and left in a dust-free environment for drying at room temperature. The resulting film was removed from the first mould, and sterilized using a 10 kGy (kilogray) electron beam. An approximately 80 µm thick transparent film of tissue dressing material essentially consisting entirely of deacetylated native chitosan acetate salt was obtained. Below, the material is referred to as tissue dressing material B.

6. Preparation of a Second Example of a Solid Film-Type Tissue Dressing Material (Material C)

The dried film from the second mould was placed for 2 hours in a bath containing a solution of 1.5% ammonia in methanol/water 90/10 (v/v). The film was then removed from the bath and dried by storage at room temperature. The film was sterilized using a 10 kGy electron beam. An approximately 80 µm thick transparent film of tissue dressing material essentially consisting entirely of deacetylated native chitosan base was obtained. Below, the material is referred to as tissue dressing material C.

7. Preparation of a Third Example of a Solid Film-Type Tissue Dressing Material (Material D1)

144 mL of the filtered solution of deacetylated chitosan prepared as above was poured into a square-shaped mould, $24\times24$ $cm^2$ in size, and left in a dust-free environment for drying at room temperature. After 3 days of storage, the resulting film was removed from the mould, transferred in a plastic bag that was then tightly sealed, and sterilized using a 25 kGy (kilogray) electron beam. An approximately 80 µm thick transparent film of tissue dressing material essentially consisting entirely of deacetylated chitosan acetate salt was obtained. Below, the material is referred to as tissue dressing material D1.

8. Preparation of a Fourth Example of a Slid Flm-Type Tissue Dressing Material (Material D2)

In a slightly modified procedure, 4% (w/w) glycerol was added to the filtered solution of deacetylated chitosan before pouring it into the square-shaped mould. Subsequent treatment as described above for tissue dressing material D1 resulted in a transparent film of tissue dressing material essentially consisting entirely of a mixture of deacetylated chitosan acetate salt and glycerol. Below, the material is referred to as tissue dressing material D2.

9. Preparation of a Fifth Example of a Solid Film-Type Tissue Dressing Material (Material D3)

In a further modified procedure, the glycerol containing solution of deacetylated chitosan was poured into a square-shaped mould which was covered with a two-layered film consisting of polyurethane/polyethylene (Platilon U073 PE, Epurex, Bomlitz/Germany), with the polyurethane side up and the polyethylene side fixed to the bottom of the mould. Subsequent treatment as described above for tissue dressing material D1 resulted in a transparent film of tissue dressing material essentially consisting entirely of a mixture of deacetylated chitosan acetate salt and glycerol which was attached to the polyurethane/polyethylene support film. Below, the material is referred to as tissue dressing material D3. Upon use, the polyethylene layer is removed. The remaining polyurethane layer is gas-permeable.

10. Preparation of a Sixth Example of a Solid Film-Type Chitosan (Chitosan D4)

In a slightly modified procedure to the preparation of chitosan film D2, 1% (w/w) glycerol was added to the filtered solution before pouring it into the square-shaped mould. Subsequent treatment as described above for chitosan D1 resulted in a transparent film essentially consisting entirely of a mixture of deacetylated chitosan acetate salt and glycerol. Below, the material is referred to chitosan D4.

11. Preparation of Two Examples of a Solid Film-Type Tissue Dressing Material with Higher DA (Materials E1 and F1)

Two further examples of tissue dressing materials were produced by the procedure leading to material D1 with the only modification that in one case the hydrolysis step was shortened, leading to a DA of 4% (material E1), and in the other case the hydrolysis step was entirely omitted, leading to a DA of 16% (material F1).

12. Water Uptake of Tissue Dressing Material C

Tissue dressing material C, produced as described in the above example, was weighted, and then placed in distilled water for 15 min. The weight of the wet film was compared to the weight of the dry film, and the water uptake was determined to be 72% by weight.

13. Water Uptake of Chitosan D4

Chitosan D4, produced as described in the above example, was weighted, and then placed in distilled water for 60 min. The weight of the wet film was compared to the weight of the dry film, and the water uptake was determined to be 1217% by weight 7 days after film preparation, and 475% by weight 14 days after film preparation.

14. Application of Tissue Dressing Materials A, B and C

In Table 1 below, the outcomes of treatments of patients with tissue dressing materials A, B and C are detailed. Material A was sprayed directly onto a wound and then left uncovered to allow the solvent to readily evaporate into the air. Materials B and C were applied as small cuts of the film-like material in direct contact with the wound. In the case of material B, the skin was pre-wetted before the application of the material. In all examples, the material was left uncovered after application.

TABLE 1

| Type of chitosan tissue dressing | Patient | Wound | Application of the dressing | Outcome |
|---|---|---|---|---|
| A | female, 49 yrs (years) | cut of 3.5 cm length and 5 mm depth (finger), moderate bleeding | application of appr. 2 mL of tissue dressing A (one treatment) | skin incision completely closed after 24 h |
| B | male, 42 yrs | cut of 1.5 cm length and 3 mm depth (hand), weak bleeding | application of tissue dressing B (size 2 × 0.5 cm$^2$) on pre-wetted skin (one treatment) | skin incision completely closed after 4 h |
| C | male, 57 yrs | praeputial inflammation | application of tissue dressing C (size 1.5 × 1.5 cm$^2$) (treatment repeated after 24 h) | Wound and ulcus completely healed after 48 h |

15. Dissolution of Chitosan Tissue Dressing

Controlled dissolution of tissue dressing materials B and C was tested in dissolution experiments using distilled water, 0.9% aqueous sodium chloride solution, and 0.5% acetic acid/acetate buffered solution, respectively. The pH of the solutions was adjusted to the values indicated in Table 2 using appropriate amounts of 1 N hydrochloric acid or sodium hydroxide solutions. Materials B and C were cut into rectangular samples having dry weights between 5 and 10 mg each. A gauze soaked with a 100-fold per volume excess of the respective solution to the dry weight of the film was applied to each sample film and the time for complete film dissolution was recorded.

TABLE 2

| pH of the dissolution mixture | Material B (distilled water) | Material B (0.9% aqueous sodium chloride) | Material C (0.9% aqueous sodium chloride) | Material C (0.5% acetic acid/acetate buffer) |
|---|---|---|---|---|
| 4.0 | n.a. | n.a. | n.d. | 0.5 h |
| 4.5 | n.a. | n.a. | n.d. | 0.5 h |
| 5.0 | n.a. | n.a. | n.d. | 2 h |
| 5.5 | 0.1 h | 0.5 h | n.d. | 4 h | n.a. = not analyzed
n.d. = no dissolution observed after 24 h

Figure 4:
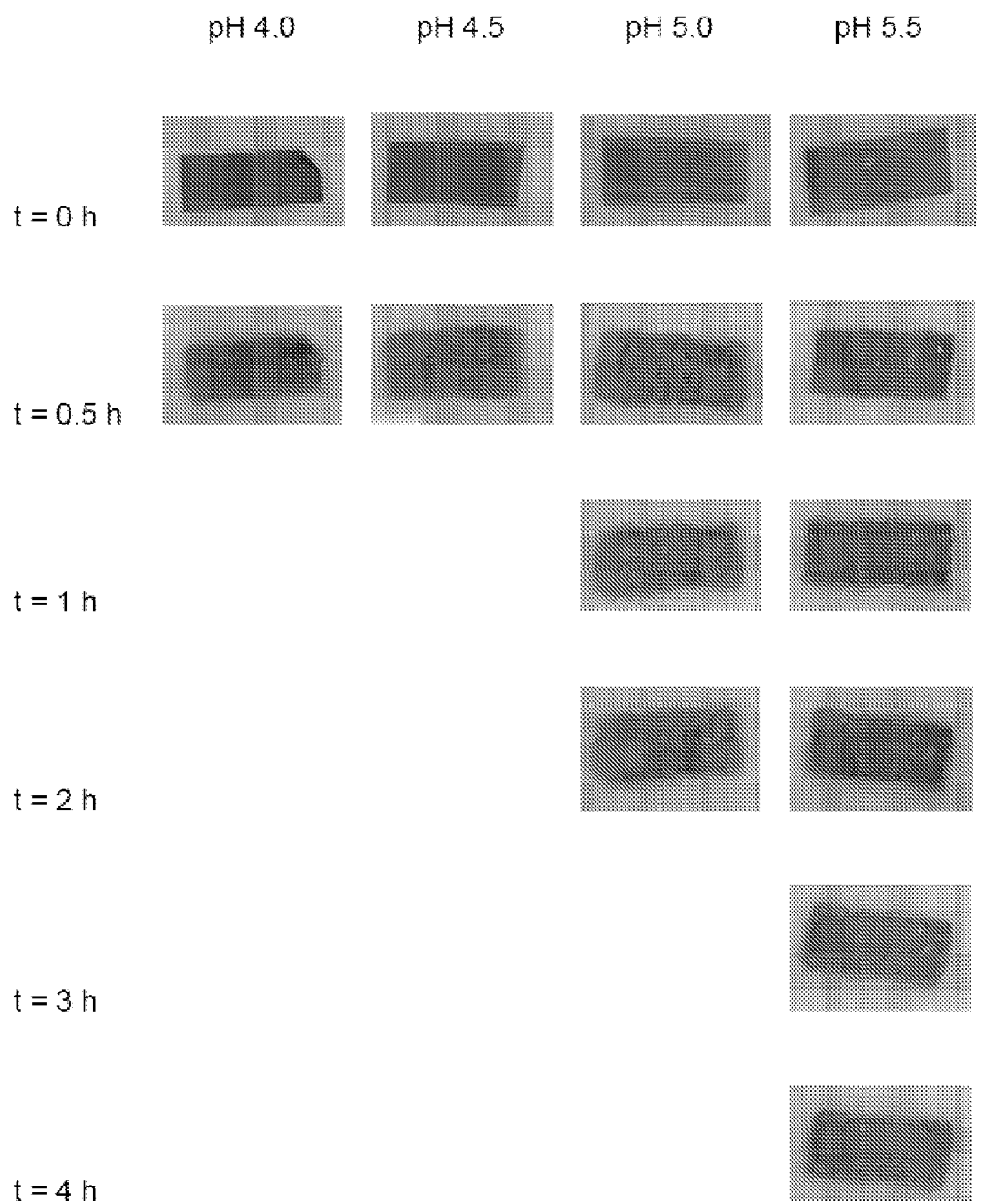
FIG. 4 illustrates the controlled dissolution of tissue dressing material according to the invention by applying a gauze soaked with acetate buffered solution.

The controlled dissolution experiment with tissue dressing material C and a mixture of 0.5% acetic acid/sodium acetate (right column in Table 2), is illustrated in FIG. 4. The material has been stained by storage in 0.01% aqueous indigocarmine solution for 1 hour for better visualization. Complete dissolution was observed after 30 minutes at pH 4.0 and 4.5, after 2 hours at pH 5.0, and after 4 hours at pH 5.5, respectively.

16. In situ Conversion of Water-Soluble Tissue Dressing Material into Water-Insoluble Tissue Dressing Material Samples of tissue dressing materials A, D1, D2, D3, and D4, respectively, were left unsealed on air at room temperature and a humidity of 20-40%. Under these conditions, tissue dressing A was drying to a solid film within several hours. Complete dissolution in distilled water was analyzed at days 3, 7, and 14. Results are summarized in Table 3.

TABLE 3

| Tissue Dressing | Day 3 | Day 7 | Day 14 |
|---|---|---|---|
| A | soluble | insoluble | insoluble |
| D1 | soluble | soluble | insoluble |
| D2 | soluble | insoluble | insoluble |
| D3 | soluble | insoluble | insoluble |
| D4 | soluble | insoluble | insoluble |

Similarly, conversion of the water-soluble into the water-insoluble form of the wound dressings A, D1, D2, D3, and D4, respectively, was observed after application of the wound dressing on human skin. In the case of D3, the wound dressing was applied to the skin with its chitosan side. Conversion of the water-soluble into the water-insoluble form of the wound dressings A, D1, D2, D3, and D4, respectively, was also observed after alkaline treatment or storage in an alkaline atmosphere.

17. Dissolution of Tissue Dressing Material with Detachment Solvent

Tissue dressing materials D1, E1 and F1 were dissolved by storage in a 2% acetic acid/acetate buffered solution. The pH of the solutions was adjusted to the values indicated in Table 4 using appropriate amounts of 10% sodium hydroxide solutions. Films D1, E1 and F1 made from chitosans with different degrees of acetylation (DA) were left on air for 14 days for conversion into the water-insoluble form, cut into rectangular samples of 1×1 cm$^2$ size and stored in approximately 10 mL of the respective solution, and the time for complete film dissolution was recorded.

TABLE 4

| pH | DA = 16% | DA = 4% | DA = 1.5% |
|---|---|---|---|
|  | Time for complete dissolution (min) | | |
| 4.0 | 5 | 10 | 1 |
| 4.5 | 15 | 15 | 2 |
| 5.0 | 30 | 15 | 15 |
| 5.5 | 60 | 60 | 30 |
| 6.0 | 60 | overnight | overnight |

Figure 5A:
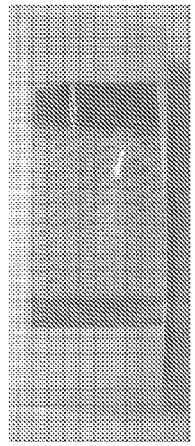
FIG. 5 shows a tissue dressing comprising a tissue dressing material according to the invention before (5a), during (5b), and after (5c) the application of the detachment solvent.
Figure 5B:
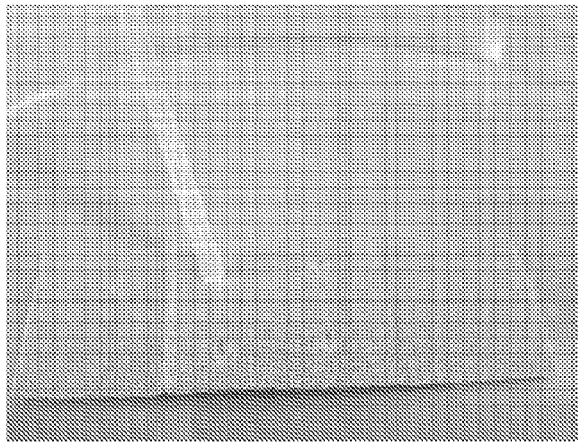
Figure 5C:
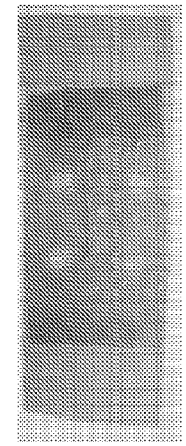

In another dissolution experiment, a wound dressing material film C (3×1 cm$^2$) was fixed on the inside of a commercial perforated band-aid (5×2 cm) which was then fixed on a Petri dish. An acetic acid/acetate buffered solution (pH 5.5) was added dropwise through the perforations of the band-aid causing the wound dressing material film to dissolve. The side of the tissue dressing comprising the tissue dressing material film is shown in FIG. 5a before and in FIG. 5c after application of the solution. The application of the solution to the band-aid side of the wound dressing is shown in FIG. 5b.

Figure 6:
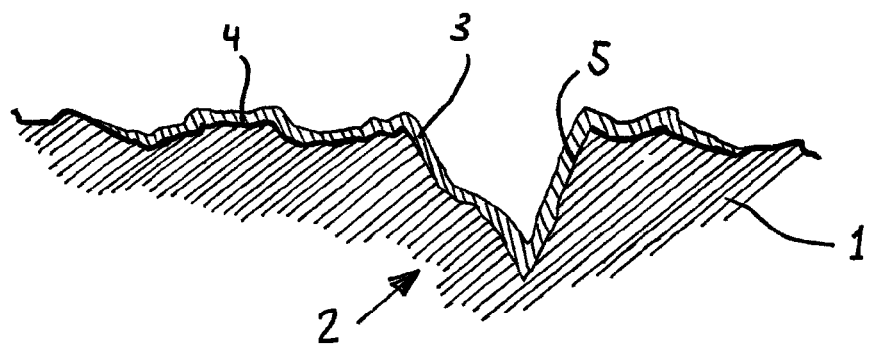
FIG. 6 schematically illustrates a wound to which a liquid tissue dressing material according to the inventions has been applied.

In FIG. 6, schematically a tissue 1 comprising a wound 2 is shown. For better illustration, FIGS. 5 to 8 are not drawn to scale. The liquid tissue dressing material according to the invention has been applied to the tissue 2 and the constituent water has been allowed to evaporate, leaving behind a film 3 that dresses the tissue 2 including the wound 3. In general, the film 3 is about 10 to 20 µm thick. Advantageously, the film 3 tightly snuggles to the tissue surface 4, including the wound surface 5.

Figure 7:
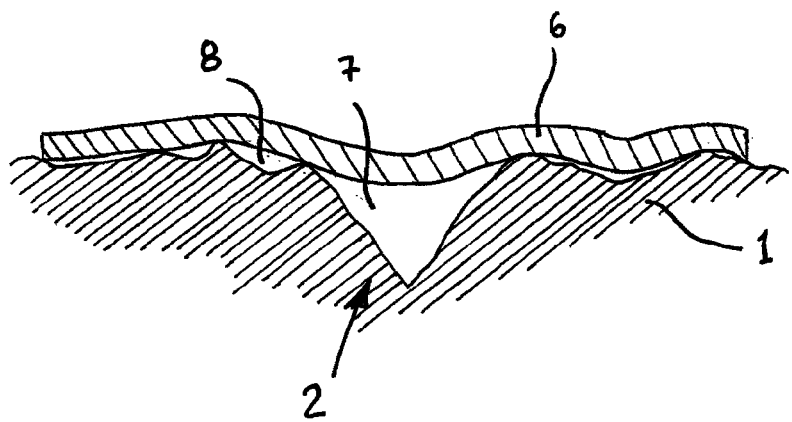
FIG. 7 schematically illustrates a wound to which a solid tissue dressing material according to the inventions has been applied.

FIG. 7 schematically shows a tissue dressing material in the form of a solid film 6 that is applied to a tissue 1, comprising a wound 2. The solid film is about 80 µm thick. Cavities 7, 8 between the tissue 1 and the tissue dressing material 6 may be filled with water or exudative fluid.

Figure 8:
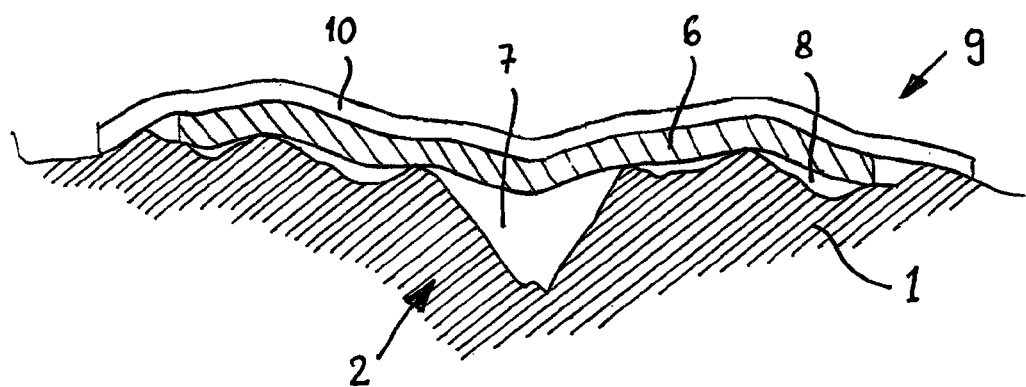
FIG. 8 schematically illustrates a wound to which a non-perforated wound dressing according to the invention has been applied.
Figure 9:
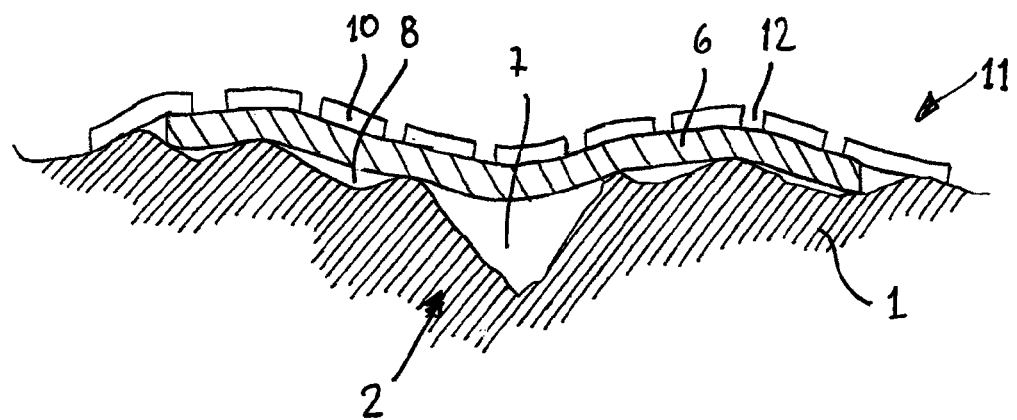
FIG. 9 schematically illustrates a wound to which a perforated wound dressing according to the invention has been applied.

In FIG. 8, a tissue dressing 9 comprising a tissue dressing material 6 of FIG. 7 as a first layer and a silicon film 10 as a second layer is applied to a tissue 1, comprising a wound 2. The silicon film 10 is about 50 µm tick. Again, cavities 7, 8 between the tissue 1 and the tissue dressing material 6 may be filled with water or exudative fluid. Finally, FIG. 9 shows a tissue dressing 11 applied to a tissue 1 comprising a wound 2, the tissue dressing 11 differing from that 9 of FIG. 8 in that the silicon film 10 is perforated to allow an exchange of air between the tissue 1 and the surrounding though the wound dressing material 6. The perforations have a diameter if between 50 and 100 µm.

18. Preparation of an Example of a Liquid-Type Tissue Dressing Material 1000 ml of tissue dressing material A was diluted by addition of 1000 mL of sterile distilled water, resulting in a liquid-type tissue dressing material consisting of 0.75% chitosan, 0.25% acetic acid and 99% water. Using a mechanical dispenser, 20 mL of the solution was each filled into glass bottles which were then equipped with a pump head, resulting in a gas-free chitosan-based wound spray. Similarly, the liquid-type dressing material was placed into a spraying apparatus containing a pressurized gas.

The features described in the above description, claims and figures can be relevant to the invention in any combination. The reference numerals in the claims have merely been introduced to facilitate reading of the claims and are by no means meant to be limiting.

What is claimed is:

1. A method for treating a tissue of a patient, the method comprising:
    applying a water-soluble solid tissue dressing material or a water soluble gel-like tissue dressing material in contact with the patient's tissue, wherein the tissue dressing material comprises chitosan with a degree of acetylation of less than 2.5%; and
    allowing the water-soluble solid tissue dressing material or the water soluble gel-like tissue dressing material to convert into a form in which it is insoluble in water at neutral pH.

2. The method of claim 1, comprising:
    after allowing the water-soluble solid tissue dressing material or the water soluble gel-like tissue dressing material to convert into a form in which it is insoluble in water at neutral pH, applying an acidic detachment solvent for removing tissue dressing material from the tissue to the water-soluble solid tissue dressing material or the water soluble gel-like tissue dressing material by at least partly dissolving the water-soluble solid tissue dressing material or the water soluble gel-like tissue dressing material.

\* \* \* \* \*